US00PP35499P2

(12) United States Plant Patent
Koning

(10) Patent No.: US PP35,499 P2
(45) Date of Patent: Nov. 21, 2023

(54) ***LAVANDULA* PLANT NAMED 'ANOUK DELUXE 1939'**

(50) Latin Name: *Lavandula stoechas*
Varietal Denomination: Anouk Deluxe 1939

(71) Applicant: L. KONING BEHEER B.V., Nuis (NL)

(72) Inventor: Lammert Koning, Nuis (NL)

(73) Assignee: L. KONING BEHEER B.V., Nuis, NJ (US)

( * ) Notice: Subject to any disclaimer, the term of this patent is extended or adjusted under 35 U.S.C. 154(b) by 0 days.

(21) Appl. No.: 18/115,696

(22) Filed: Feb. 28, 2023

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 6/502; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Lavandula* plant named 'Anouk Deluxe 1939', characterized by its compact and upright plant habit; freely branching growth habit; freely flowering habit; dark violet-colored flowers and bright purple-colored terminal flower bracts positioned on strong and erect peduncles; long flowering period; and good garden performance.

2 Drawing Sheets

Figure 1:
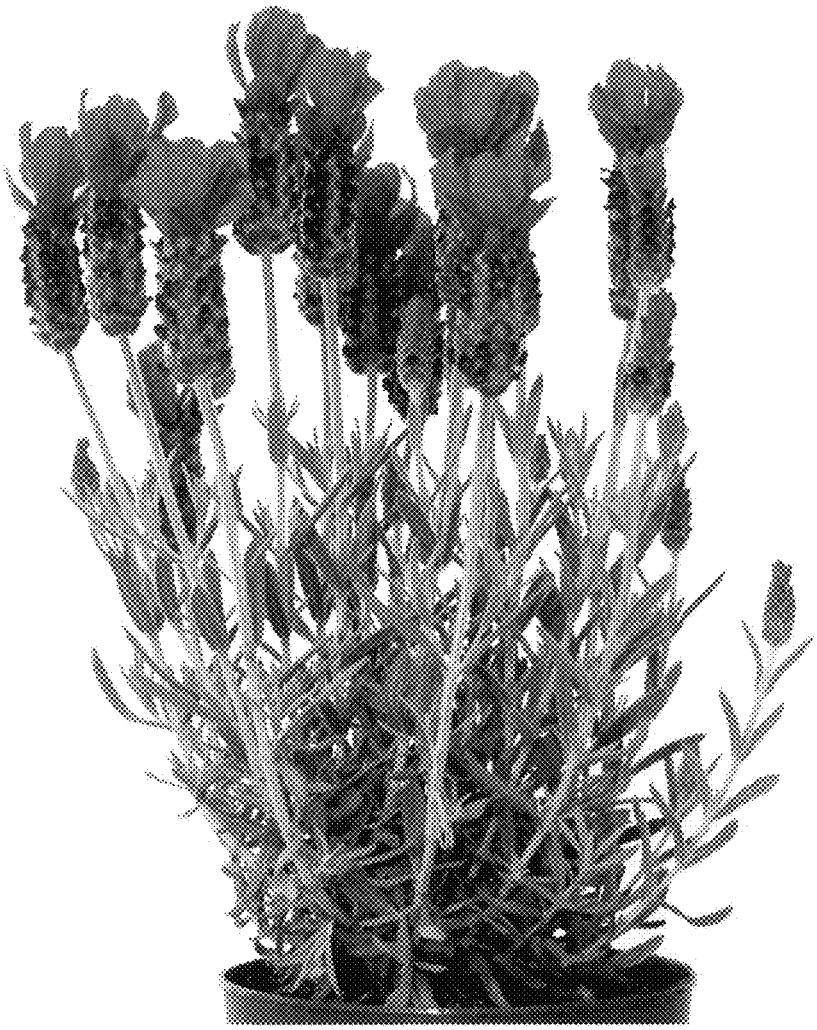

Botanical designation: *Lavandula stoechas.*
Cultivar denomination: 'ANOUK DELUXE 1939'.

STATEMENT REGARDING PRIOR DISCLOSURES BY APPLICANT

An European Plant Breeder's Rights application for the instant plant was filed by the Applicant on Jun. 30, 2022, application number 2022/1630. Foreign priority is not claimed to this application.

BACKGROUND OF THE INVENTION

The present invention relates to a new and distinct *Lavandula* plant, botanically known as *Lavandula stoechas*, commonly referred to as Lavender and hereinafter referred to by the name 'Anouk Deluxe 1939'.

The new *Lavandula* plant is a product of a planned breeding program conducted by the Inventor in Boskoop, The Netherlands. The objective of the breeding program was to develop new unique *Lavandula* plants with good performance and attractive plant fotm and flower coloration.

The new *Lavandula* plant originated from a cross-pollination in May, 2018 of *Lavandula stoechas* 'Anouk Deluxe 169', disclosed in U.S. Plant Pat. No. 28,851, as the female, or seed, parent with a proprietary selection of *Lavandula stoechas* identified as code number 1803, not patented, as the male, or pollen, parent. The new *Lavandula* plant was discovered and selected by the Inventor as a single flowering plant within the progeny of the stated cross-pollination in a controlled environment in Boskoop, The Netherlands in July, 2019.

Asexual reproduction of the new *Lavandula* plant by terminal cuttings in a controlled greenhouse environment in Boskoop, The Netherlands since September, 2019 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Anouk Deluxe 1939' as a new and distinct *Lavandula* plant:

1. Compact and upright plant habit.
2. Freely branching growth habit.
3. Freely flowering habit.
4. Dark violet-colored flowers and bright purple-colored terminal flower bracts positioned on strong and erect peduncles.
5. Long flowering period.
6. Good garden performance.

Plants of the new *Lavandula* differ primarily from plants of the female parent, 'Anouk Deluxe 169', primarily in the following characteristics:

1. Plants of the new *Lavandula* have more terminal flower bracts than plants of 'Anouk Deluxe 169'.
2. Plants of the new *Lavandula* have bright purple-colored terminal flower bracts whereas plants of 'Anouk Deluxe 169' have red purple to purple-colored tetminal flower bracts.
3. Plants of the new *Lavandula* will rebloom whereas plants of 'Anouk Deluxe 169' rarely rebloom.

Plants of the new *Lavandula* differ primarily from plants of the male parent selection primarily in the following characteristics:

1. Plants of the new *Lavandula* are more upright than plants of the male parent selection.
2. Plants of the new *Lavandula* have more terminal flower bracts than plants of the male parent selection.

Plants of the new *Lavandula* can be compared to plants of the *Lavandula stoechas* 'Anouk', disclosed in U.S. Plant Pat. No. 16,685. In side-by-side comparisons, plants of the new *Lavandula* differ primarily from plants of 'Anouk' in the following characteristics:

1. Plants of the new *Lavandula* are more compact and more upright than plants of 'Anouk'.
2. Leaves of plants of the new *Lavandula* are broader and more greyish green in color than leaves of plants of 'Anouk'.
3. Plants of the new *Lavandula* have more terminal flower bracts than plants of 'Anouk'.
4. Plants of the new *Lavandula* have darker and brighter purple-colored terminal flower bracts than plants of 'Anouk'.
5. Plants of the new *Lavandula* will rebloom whereas plants of 'Anouk Deluxe' rarely rebloom.

Plants of the new *Lavandula* can also be compared to plants of the *Lavandula stoechas* 'Toscane', disclosed in U.S. Plant Pat. No. 18,046. In side-by-side comparisons, plants of the new *Lavandula* differ primarily from plants of 'Toscane' in the following characteristics:

1. Plants of the new *Lavandula* are more compact and more upright than plants of 'Toscane'.
2. Leaves of plants of the new *Lavandula* are broader and more greyish green in color than leaves of plants of 'Toscane'.
3. Plants of the new *Lavandula* have more terminal flower bracts than plants of 'Toscane'.
4. Plants of the new *Lavandula* have darker and brighter purple-colored terminal flower bracts than plants of 'Toscane'.
5. Plants of the new *Lavandula* will rebloom whereas plants of 'Toscane' rarely rebloom.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors ofthe new *Lavandula* plant.

The photograph on the first sheet (FIG. 1) is a side perspective view of a typical flowering plant of 'Anouk Deluxe 1939' grown in a container.

Figure 2:
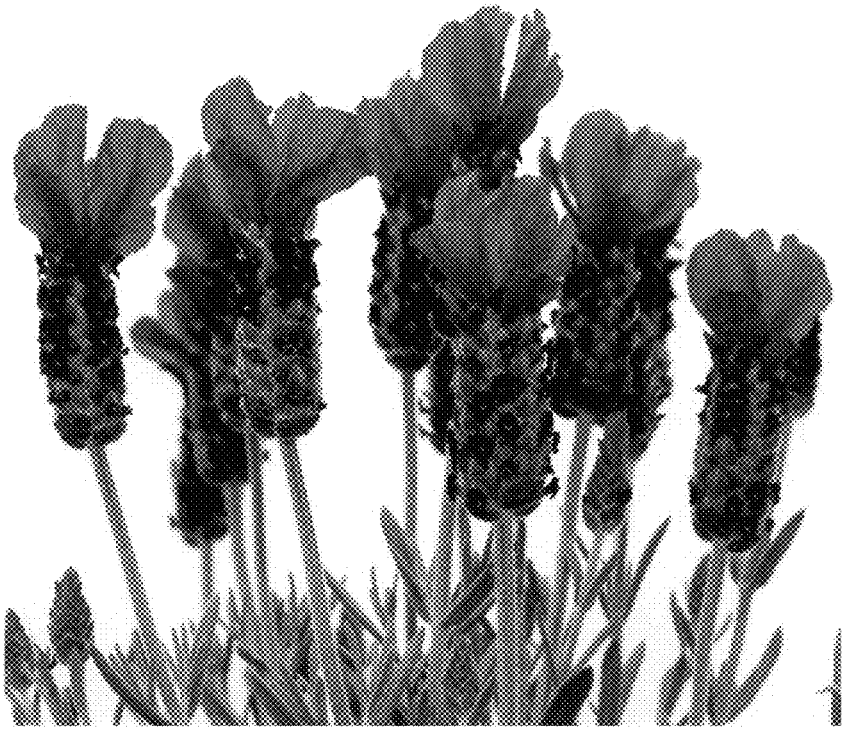

The photograph on the second sheet (FIG. 2) is a close-up view of a typical flowering plant of 'Anouk Deluxe 1939'.

DETAILED BOTANICAL DESCRIPTION

Plants used in the aforementioned photographs and following detailed description were grown in 12-cm containers during the spring in an outdoor nursery in Boskoop, The Netherlands and under cultural practices typical of commercial *Lavandula* production. Plants were pinched one time and were nine months old when the photographs and description were taken. During the production of the plants, day temperatures ranged from 10C to 30C and night temperatures ranged from 5C to 20C. In the following description, color references are made to The Royal Horticultural Society Colour Chart, 2015 Edition, except where general tetins of ordinary dictionary significance are used.

Botanical classification: *Lavandula stoechas* 'Anouk Deluxe 1939'.

Parentage:

*Female, or seed, parent.*—*Lavandula stoechas* 'Anouk Deluxe 169', disclosed in U.S. Plant Pat. No. 28,851.

*Male, or pollen, parent.*—Proprietary selection of *Lavandula stoechas* identified as code number 1803, not patented.

Propagation:

*Type.*—Terminal vegetative cuttings.

*Time to initiate roots, summer and winter.*—About ten days at temperatures about 18C.

*Time to produce a rooted young plant, summer.*—About 60 days at temperatures about 20C.

*Time to produce a rooted young plant, winter.*—About 70 days at temperatures about 20C.

*Root description.*—Fine, fibrous; initially white in color and becoming more brown with development; actual color of the roots is dependent on substrate composition, water quality, fertilizer type and fottnulation.

*Rooting habit.*—Freely branching; dense.

Plant description:

*Plant and growth habit.*—Herbaceous perennial; compact and upright plant habit; narrowly obovate in overall plant shape; freely branching habit; moderately vigorous growth habit; oderate growth rate; flowers arranged in verticillasters on crowded spikes with showy terminal flower bracts.

*Plant height, soil level to top of foliar plane.*—About 16.2 cm.

*Plant height, soil level to top of floral plane.*—About 23.1 cm.

*Plant width.*—About 20 cm.

*Lateral branch description.*—Quantity per plant: About eight primary lateral branches each with about four secondary lateral branches developing per plant; pinching enhances branching potential. Length: About 7.7 cm. Diameter: About 2 mm. Internode length: About 1.4 cm. Strength: Moderately strong. Aspect: Primary lateral branches, upright to about 40 degrees from vertical; secondary lateral branches, about 35 degrees from primary lateral branch axis. Texture and luster: Densely tomentose; slightly glossy. Color, when developing: Close to 145B. Color, developed: Close to 144B and 145A; with development, close to 200D.

*Leaf description.*—Arrangement: Opposite, simple; sessile. Length: About 3.15 cm. Width: About 6 mm. Shape: Narrowly oblanceolate to narrowly lanceolate and narrowly oblong. Apex: Acute. Base: Cuneate. Margin: Entire; moderately revolute; not lobed. Texture and luster, upper surface: Densely tomentose; not rugose; matte. Texture and luster, lower surface: Densely tomentose; slightly rugose; matte. Fragrance: Strongly aromatic, pungent. Venation pattern: Pinnate. Color: Developing leaves, upper surface: Close to 138A. Developing leaves, lower surface: Close to 138B. Fully expanded leaves, upper surface: Close to NN137D; venation, close to 146D.

Fully expanded leaves, lower surface: Close to 147B; venation, close to 147C.

Flower description:

*Flower type, arrangement and habit.*—Small single salverform flowers arranged in compact verticillasters on crowded terminal spikes; freely flowering, about 150 flowers developing per inflorescence and about 5,200 flowers developing per plant; flowers with two-lobed upper lip and three-lobed lower lip; flowers face mostly outwardly on the spike; inflorescences with showy terminal flower bracts.

*Natural flowering season.*—Long flowering period; continuous from late spring into the summer in The Netherlands; plants reblooming for about ten weeks.

*Flower longevity on the plant.*—Individual flowers last about four weeks on the plant; flowers not persistent.

*Fragrance.*—None detected.

*Flower buds.*—Length: About 6 mm. Diameter: About 1.5 mm. Shape: Oblong. Texture and luster: Densely tomentose; matte. Color: Close to 145C; distally, close to 146B tinged with close to N186B and at the apex, close to N77B.

*Inflorescence size.*—Height, including terminal flower bracts: About 5.8 cm. Height, excluding tetrminal flower bracts: About 3.5 cm. Diameter, at tel flower bracts: About 3.1 cm. Diameter, below flower bracts: About 1.8 cm.

*Flower size.*—Diameter: About 3.5 mm by 3.5 mm. Depth (height): About 9 mm. Throat diameter: About 1.25 mm. Tube length: About 6 mm. Tube diameter: About 1 mm.

*Petals.*—Quantity and arrangement: Upper lip, two-lobed and lower lip, three-lobed. Length, upper lip: About 3 mm. Length, lower lip: About 2 mm. Width, upper lip: About 2 mm. Width, lower lip: About 2 mm. Shape: Roughly spatulate; lower 66% fused into a tube. Apex: Obtuse. Margin: Entire; moderately undulate. Texture and luster, upper surface: Smooth, glabrous; moderately velvety; not rugose; matte. Texture and luster, lower surface: Smooth, glabrous; slightly velvety; not rugose; matte. Texture, throat: Smooth, glabrous; slightly velvety. Texture, tube: Smooth, glabrous. Color: When opening and fully opened, upper surface: Slightly darker than N92D; venation, slightly darker than N92D; color becoming closer to N186B with subsequent development. When opening and fully opened, lower surface: Close to N92D; venation, close to N92D; color becoming closer to N186B with subsequent development. Throat: Close to between 90A and N92D; venation, close to between 90A and N92D. Tube: Close to 86A fading proximally to close to N155A; venation, close to 86A and N155A.

*Terminal flower bracts.*—Quantity and arrangement: About twelve positioned mostly upright at inflorescence apex. Length: About 2.2 cm. Width: About 1.1 cm. Shape: Obovate to narrowly obovate. Apex: Obtuse to bluntly acute. Base: Acuminate. Margin: Entire; moderately and finely undulate. Texture and luster, upper and lower surfaces: Sparsely tomentose; matte. Color, upper surface: Close to N81A to N81B; midvein, close to 200B. Color, lower surface: Close to N81A to N81B; midvein, close to N79B.

*Basal flower bracts.*—Quantity and arrangement: Each group of seven flowers is subtended by a single basal flower bract. Length: About 6 mm. Width: About 9 mm. Shape: Broadly reniform. Apex: Abruptly acute. Base: Truncate. Margin: Entire. Texture and luster, upper surface: Moderately tomentose; slightly glossy. Texture and luster, lower surface: Moderately tomentose; matte. Color, upper surface: Close to N79C; venation, close to 146Ad. Color, lower surface: Close to N79C; venation, close to between N186A and N200A.

*Sepals.*—Quantity and arrangement: Five, fused into a campanulate tube. Calyx length: About 5.5 mm. Calyx diameter: About 1.75 mm. Length: About 5.5 mm. Width: About 0.75 mm. Shape: Linear. Apex: Acute. Margin: Entire. Texture and luster, upper surface: Smooth, glabrous; glossy. Texture and luster, lower surface: Densely tomentose; slightly glossy. Color: When opening, upper surface: Close to 145C to 145D; distally, moderately tinged with close to N186B; venation, close to 144B. When opening, lower surface: Close to 145C; distally, close to 146B tinged with close to N186B and at the apex, close to N77B. Fully opened, upper surface: Close to 145C to 145D; distally, moderately tinged with close to N186B; venation, close to 144B. Fully opened, lower surface: Close to 145B; distally, close to 146B and at the apex, close to N77B.

*Peduncles.*—Length: About 6.2 cm. Diameter: About 2 mm. Aspect: Mostly upright. Strength: Strong. Texture and luster: Densely tomentose; matte. Color: Close to 143B and 151B and distally, tinged with close to N186C.

*Reproductive organs.*—Stamens: Quantity per flower: Four. Filament length: About 1 mm. Filament color: Close to N87C. Anther shape: Short oblong; dorsifixed. Anther size: About 0.75 mm by 0.75 mm. Anther color: Close to 161D. Pollen amount: Scarce. Pollen color: Close to 16B. Pistils: Quantity per flower: One. Pistil length: About 3.5 mm. Stigma shape: Club-shaped. Stigma diameter: About 0.5 mm. Stigma color: Close to N186A. Style length: About 3.5 mm. Style color: Close to NN155A and distally, close to 76A. Ovary color: Close to 148A.

*Seeds and fruits.*—To date, seed and fruit production has not been observed on plants of the new *Lavandula*.

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain and wind and have been observed to tolerate temperatures from about 1C to about 40C and to be suitable for USDA ardiness Zones 7 to 10.

It is claimed:

1. A new and distinct *Lavandula* plant named 'Anouk Deluxe 1939' as illustrated and described.

* * * * *